United States Patent
Ikemoto et al.

(10) Patent No.: US 8,357,380 B2
(45) Date of Patent: Jan. 22, 2013

(54) COENZYME Q10-CONTAINING COMPOSITION

(75) Inventors: Hiroyuki Ikemoto, Chiyoda-ku (JP); Tsuyoshi Minemura, Ohi-machi (JP)

(73) Assignee: Nisshin Pharma Inc., Tokyo (JP)

( * ) Notice: Subject to any disclaimer, the term of this patent is extended or adjusted under 35 U.S.C. 154(b) by 0 days.

(21) Appl. No.: 13/348,335

(22) Filed: Jan. 11, 2012

(65) Prior Publication Data

US 2012/0107374 A1  May 3, 2012

Related U.S. Application Data

(63) Continuation of application No. 11/632,933, filed as application No. PCT/JP2005/015071 on Aug. 18, 2005, now Pat. No. 8,119,113.

(30) Foreign Application Priority Data

Aug. 24, 2004  (JP) .................................. 2004-243257

(51) Int. Cl.
*A61K 9/00* (2006.01)
*A61K 31/74* (2006.01)
(52) U.S. Cl. ....................................... 424/400; 424/401
(58) Field of Classification Search ................. 424/94.1, 424/648, 400, 401
See application file for complete search history.

(56) References Cited

U.S. PATENT DOCUMENTS 6,479,058 B1 * 11/2002 McCadden .................... 424/401

* cited by examiner

*Primary Examiner* — Ruth Davis
(74) *Attorney, Agent, or Firm* — Ohlandt, Greeley, Ruggiero & Perle, L.L.P.

(57) ABSTRACT

The coenzyme $Q_{10}$-containing liquid composition is obtained by dispersing and emulsifying coenzyme $Q_{10}$ in an aqueous liquid containing a water-soluble substance consisting of octenylsuccinate starch and dextrin, and glycerin. The liquid composition may be dried to prepare a coenzyme $Q_{10}$-containing solid composition.

12 Claims, No Drawings

COENZYME Q10-CONTAINING COMPOSITION

CROSS-REFERENCE TO RELATED APPLICATIONS

This application is a continuation application of U.S. patent application Ser. No. 11/632,933, filed on Jan. 19, 2007, now U.S. Pat. No. 8,119,113 which is a national phase filing of International Application No. PCT/JP2005/015071, filed on Aug. 18, 2005, which claims priority to Japanese Patent Application No. 2004-243257, filed on Aug. 24, 2004, all of which are incorporated herein in their entirety by reference thereto.

BACKGROUND

1. Field of the Disclosure

The present disclosure relates to a coenzyme $Q_{10}$-containing composition obtained by dispersing and emulsifying coenzyme $Q_{10}$ in an aqueous liquid containing a water-soluble substance and a polyhydric alcohol. More specifically, the disclosure relates to a composition obtained by dispersing and emulsifying coenzyme $Q_{10}$ in an aqueous liquid containing a water-soluble substance consisting of octenylsuccinate starch and dextrin, and glycerin as the polyhydric alcohol. The composition can contain coenzyme $Q_{10}$ at a high content, and has excellent stability and bioavailability.

2. Discussion of the Background Art

Coenzyme $Q_{10}$ is a type of coenzyme Q (molecular formula: $C_{59}H_{90}O_4$, molecular weight: 863.36) found in higher animals, and it is also known as ubidecarenone. Coenzyme $Q_{10}$ is not only bioactive as a coenzyme, but is also known as a vitamin-like substance having an effect of improving oxygen utilization efficiency. In addition to acting on congestive tissue, Coenzyme $Q_{10}$ is believed to also stabilize biological membranes and exhibit antioxidant and other effects, while it has been clinically shown to have pharmacological effects that ameliorate symptoms of angina, cardiac failure, ischemic heart disease and muscular dystrophy. It has, in addition, been reported to be effective for prevention and treatment of hypertension, arteriosclerosis, heart disease, diabetes and periodontal disease, as well as for prevention of carcinostatic or psychotropic agent side-effects, and for fatigue refreshment and motor function recovery. Coenzyme $Q_{10}$ is highly bioactive and highly safe for the human body.

In recent years, coenzyme $Q_{10}$ has been approved for use as a food, and is becoming important as a material for health foods.

However, coenzyme $Q_{10}$ is a lipophilic solid with a low melting point and hardly soluble in water. The bioavailability of orally ingested coenzyme $Q_{10}$ is therefore very low. Also, coenzyme $Q_{10}$ is unstable and decomposes under light to produce hydroquinones, ubichromenol and the like.

As a composition providing increased bioavailability of coenzyme $Q_{10}$ there has been proposed a coenzyme $Q_{10}$-containing composition obtained by preparing coenzyme $Q_{10}$ as an aqueous emulsion using a polyglycerin fatty acid ester as the emulsifier, mixing the emulsion with an aqueous solution containing a water-soluble macromolecular substance at a weight of 3-fold with respect to ubiquinone, and spray drying the mixture (JP59-51214A). There has also been proposed production of fat-soluble substance aqueous liquid formulations, by emulsification of a fat-soluble substance such as coenzyme $Q_{10}$ with an emulsifier such as a glycerin fatty acid ester, sucrose fatty acid ester, polyoxyethylene sorbitan fatty acid ester, polyoxyethylene hydrogenated castor oil or the like, a polyhydric alcohol and water (JP2000-212066A). In addition, there has been proposed production of a coenzyme $Q_{10}$-containing emulsified composition obtained from coenzyme $Q_{10}$ using an oil-phase component such as a vegetable oil or fatty acid ester, a polyhydric alcohol, and an emulsifier such as a glycerin fatty acid ester (JP2003-238396A). However, because emulsifiers such as glycerin fatty acid esters and sucrose fatty acid esters are highly viscous liquid substances, it is necessary to add large amounts of excipients to obtain solid compositions from the emulsions obtained using such emulsifiers, and this not only limits the coenzyme $Q_{10}$ content but also lowers manageability as a result of sticking and other problems during the drying step. Moreover, using such emulsifiers can also impair the taste and texture of food products, depending on the form used. In addition, since most of such emulsifiers are synthetic products they are sometimes undesirable for use. JP2003-238396A mentions water-soluble macromolecules such as starch, dextrin and gum arabic as emulsifiers, but emulsified compositions using these water-soluble macromolecules instead of synthetic emulsifiers have not been produced, and it is unknown whether a stable coenzyme $Q_{10}$-containing emulsion can be obtained by this method.

On the other hand, for dispersing and emulsifying coenzyme $Q_{10}$ without using glycerin fatty acid esters or other synthetic emulsifiers, there is a method of dispersing and emulsifying coenzyme $Q_{10}$ in an aqueous liquid containing a water-soluble substance such as gum arabic, agar, water-soluble corn fiber, starch, gelatin, xanthan gum, casein, dextrin or the like in the presence of an organic acid (JP 2003-55203A). This method can provide products with high bioavailability and stability, but products with even higher coenzyme $Q_{10}$ contents are desired.

There is a method for producing emulsified powders by adding processed starch, saccharides and water to fat-soluble substances for emulsification and then drying the mixtures, and emulsified powdered products have been disclosed that contain about 52% tocopherol acetate (JP11-196785A). Still, the compositions obtained when this method is applied to coenzyme $Q_{10}$ are unsatisfactory from the standpoint of emulsion stability.

Thus, a high demand remains for a coenzyme $Q_{10}$-containing composition that employs no glycerin fatty acid esters or other synthetic emulsifiers, that can include a high content of coenzyme $Q_{10}$, and that can provide high stability and bioavailability for coenzyme $Q_{10}$.

SUMMARY

It is an object of the present disclosure to provide a coenzyme $Q_{10}$-containing composition that employs no synthetic emulsifiers such as glycerin fatty acid esters, polyglycerin fatty acid esters, organic acid monoglycerides, propylene glycol fatty acid esters, sorbitan fatty acid esters or sucrose fatty acid esters, that can include a high content of coenzyme $Q_{10}$, and that can provide high stability and bioavailability for coenzyme $Q_{10}$.

As a result of much diligent research directed toward solving the problems described above, the present inventors have found that by using a composition obtained by dispersing and emulsifying coenzyme $Q_{10}$ in an aqueous liquid containing a water-soluble substance and a polyhydric alcohol, it is possible to produce a coenzyme $Q_{10}$-containing composition with excellent stability and bioavailability even with a high coenzyme $Q_{10}$ content. In particular, a highly superior coenzyme $Q_{10}$-containing composition can be obtained by using a combination of octenylsuccinate starch and dextrin as the water-soluble substance and glycerin as the polyhydric alcohol. In other words, the present disclosure relates to a coenzyme $Q_{10}$-containing liquid composition obtained by dispersing and emulsifying coenzyme $Q_{10}$ in an aqueous liquid containing specific amounts of a water-soluble substance consisting of octenylsuccinate starch and dextrin, and glycerin. By drying the coenzyme $Q_{10}$-containing liquid composition it is possible to produce a coenzyme $Q_{10}$-containing solid composition. A carrier may be used if necessary at the time of drying.

The coenzyme $Q_{10}$-containing composition of the disclosure is a composition having a high coenzyme $Q_{10}$ content while also exhibiting very high bioavailability whereby the coenzyme $Q_{10}$ is reliably absorbed even when ingested on an empty stomach. Thus, the coenzyme $Q_{10}$-containing composition of the disclosure has a very wide range of applications as a material for production of various forms of pharmaceuticals and foods with high coenzyme $Q_{10}$ contents, or as a material for addition to various foods, feeds or cosmetics.

DETAILED DESCRIPTION OF THE PREFERRED EMBODIMENT

The coenzyme $Q_{10}$-containing liquid composition of the disclosure is prepared by dispersing and emulsifying coenzyme $Q_{10}$ in an aqueous liquid containing specific amounts of a water-soluble substance consisting of octenylsuccinate starch and dextrin, and glycerin. More specifically, it is an aqueous liquid obtained by dispersing and emulsifying 1-50 wt % of coenzyme $Q_{10}$ in an aqueous liquid containing 0.01-10 wt % of glycerin, 4-30 wt % of a water-soluble substance consisting of octenylsuccinate starch and dextrin, and 40-94 wt % of water.

By drying the coenzyme $Q_{10}$-containing liquid composition it is possible to produce a coenzyme $Q_{10}$-containing solid composition. A carrier may be used if necessary at the time of drying. A coenzyme $Q_{10}$-containing solid composition obtained by drying the aforementioned coenzyme $Q_{10}$-containing liquid composition without using a carrier contains 3-80 wt % of coenzyme $Q_{10}$, 0.01-25 wt % of glycerin and 19-96 wt % of a water-soluble substance consisting of octenylsuccinate starch and dextrin. The solid composition may be placed in water to restore the liquid composition in the condition before drying.

In the coenzyme $Q_{10}$-containing liquid composition of the disclosure, the dispersed and emulsified coenzyme $Q_{10}$ particles, and specifically the dispersed and emulsified particles containing coenzyme $Q_{10}$, have a mean particle size of no greater than 3 μm, more preferably no greater than 1 μm and even more preferably no greater than 0.8 μm. The mean particle size as an aqueous dispersion is stably maintained when the liquid composition is stored for prolonged periods.

The coenzyme $Q_{10}$ emulsified particles in a liquid composition obtained by resuspending or dissolving the coenzyme $Q_{10}$-containing solid composition in an aqueous liquid likewise have a mean particle size of no greater than 3 μm, more preferably no greater than 1 μm and even more preferably no greater than 0.8 μm. This also applies when the liquid composition is directly dried or when it is adsorbed onto or supported on a carrier. The mean particle size is stably maintained even when the solid composition is stored for prolonged periods and then redissolved or redispersed in an aqueous liquid.

The coenzyme $Q_{10}$ content in the composition of the disclosure may be appropriately set depending on the desired dosage and the form of the composition, but for a liquid it is in the range of 0.001-50 wt % and preferably about 0.01-10 wt %. When the form is a solid form such as powder or granules, the content is generally in the range of 0.01-80 wt % and preferably 0.5-60 wt %, such as about 50 wt %, for example. The amount of coenzyme $Q_{10}$ to be ingested per day will differ depending on age, body weight and state of health, and may be 5-600 mg/day and preferably 10-300 mg/day for healthy adults.

The water-soluble substance used for dispersion and emulsification of the coenzyme $Q_{10}$ acts as a protective colloid, dispersing and emulsifying the coenzyme $Q_{10}$ as homogeneous fine particles to maintain a stable emulsion. As water-soluble substances there may be mentioned gum arabic, various starches, gelatin, xanthan gum, casein, carmellose sodium (CMC sodium), guar gum, pullulan, carrageenan, polyvinylpyrrolidone (PVP), polyvinyl alcohol (PVA), carboxyvinyl polymer, methyl cellulose, ethyl cellulose, hydroxypropyl cellulose and vegetable-derived water-soluble polysaccharides such as pectin. In order to obtain a stable emulsion containing homogeneous, fine coenzyme $Q_{10}$ particles, however, a combination of octenylsuccinate starch and dextrin is optimal.

As starting materials for octenylsuccinate starch there may be mentioned starches such as tapioca starch, potato starch, corn starch, waxy corn starch, rice starch and wheat starch. As dextrins there may be mentioned hydrolysates of the aforementioned starches, and malt dextrin and the like.

The content of the water-soluble substance consisting of octenylsuccinate starch and dextrin in the coenzyme $Q_{10}$-containing composition of the disclosure will differ depending on the form of the composition (liquid or solid) and the coenzyme $Q_{10}$ content. For a liquid composition, it may be in the range of 4-30 wt % and preferably 10-20 wt % based on the weight of the composition. For a solid composition, it may be in the range of 19-96 wt % and preferably 30-90 wt %. The proportion of addition of the octenylsuccinate starch and dextrin in the water-soluble substance may be in the range of 5-95:95-5 and preferably 25-80:75-20 based on weight. If the proportion of addition of the octenylsuccinate starch and dextrin is outside of this range, the effect of their combination will be reduced and it will not be possible to obtain the intended coenzyme $Q_{10}$-containing composition, i.e. a homogeneous, fine, stable emulsion.

As polyhydric alcohols there may be mentioned glycerin, propylene glycol, polyethylene glycol, sugar alcohols (for example, sorbitol, erythritol, mannitol, xylitol, etc.) and sugars such as glucose, fructose, sucrose, maltose and the like, but glycerin is most optimal in order to obtain a homogeneous, fine, stable coenzyme $Q_{10}$-containing emulsion. A sufficient effect can be achieved when using food-grade glycerin as well as when using pharmaceutical-grade glycerin. The glycerin content will differ depending on the composition form (liquid or solid) and the coenzyme $Q_{10}$ content, but for a liquid composition it may be in the range of 0.01-10 wt % and preferably 0.5-5 wt % based on the weight of the composition. For a solid composition, it may be in the range of 0.01-25 wt % and preferably 0.1-10 wt %.

In order to obtain the desired coenzyme $Q_{10}$-containing composition according to the disclosure, it is essential to combine the three components, i.e. glycerin and the water-soluble substance consisting of octenylsuccinate starch and dextrin, during dispersion and emulsification of the coenzyme $Q_{10}$. If any of these three components is absent or replaced with another component, it will either be impossible to obtain the intended homogeneous, fine, stable coenzyme $Q_{10}$-containing emulsion, or problems may occur with storage stability of the emulsified particles or bioavailability of the coenzyme $Q_{10}$.

Although octenylsuccinate starch and dextrin are used as the water-soluble substance when the coenzyme $Q_{10}$ of the disclosure is dispersed and emulsified, other water-soluble substances such as gum arabic and the like may also be added in a range that does not prevent the effect.

During production of the coenzyme $Q_{10}$-containing composition of the disclosure, an organic acid may also be added to the aqueous liquid to stabilize the coenzyme $Q_{10}$, either before or after dispersion and emulsification of the coenzyme $Q_{10}$ in the aqueous liquid. Examples of organic acids include citric acid, succinic acid, fumaric acid, lactic acid, gluconic acid, malic acid, tartaric acid and their salts, among which there are preferred citric acid, malic acid, tartaric acid or their salts, and mixtures thereof. As examples of organic acid salts there may be mentioned sodium salts, potassium salts, magnesium salts and calcium salts. The amount of organic acid added will differ depending on the type of organic acid, but generally it will be in the range of 0.01-30 wt % and preferably 0.05-15 wt % based on the weight of the composition.

Thus, a liquid composition with addition of an organic acid contains 1-50 wt % of coenzyme $Q_{10}$, 0.01-10 wt % of glycerin, 4-30 wt % of a water-soluble substance, 0.01-10 wt % of an organic acid and 40-94 wt % of water. A solid composition with addition of an organic acid contains 3-80 wt % of coenzyme $Q_{10}$, 0.01-25 wt % of glycerin, 19-96 wt % of a water-soluble substance and 0.01-30 wt % of an organic acid. The composition with addition of an organic acid may be used, either alone or after dilution or concentration, as a food material, pharmaceutical material, cosmetic material or feed additive.

During preparation of the coenzyme $Q_{10}$-containing composition, the coenzyme $Q_{10}$ as the fat-soluble agent is first melted, and then dispersed and emulsified in an aqueous liquid containing the glycerin and specific water-soluble substance, to form a fine particle emulsion. Thus, preferably an aqueous solution of the glycerin and water-soluble substance is prepared and pre-heated. The coenzyme $Q_{10}$ that has been already heated and melted is introduced into the aqueous solution, and then finely dispersed and emulsified to the desired mean particle size by publicly known means such as a high-pressure homogenizer to form a homogeneous, fine emulsion. These steps are preferably carried out at a higher temperature than the melting point of coenzyme $Q_{10}$, such as about 45-90° C. and preferably 50-70° C. Alternatively, coenzyme $Q_{10}$ may be directly added and dispersed in an aqueous solution that has been preheated (about 45-90° C. and preferably 50-70° C.), dissolved in the solution and then emulsified. This method is preferred for more efficient workability and to avoid loss of the starting materials. For dispersion and emulsification of the coenzyme $Q_{10}$, the coenzyme $Q_{10}$ may be dissolved in or mixed with a fat or oil or an edible oil, and an organic acid may be added during preparation of the aqueous solution for stabilization of the coenzyme $Q_{10}$.

The specific water-soluble substance used for the disclosure keeps the fine emulsified particles of coenzyme $Q_{10}$ stable from the time of production of the composition of the disclosure until its ingestion and absorption, and thus provides the advantage of promoting its uptake into the body.

When the coenzyme $Q_{10}$-containing liquid composition of the disclosure is dried for solidification, any drying and solidification methods common for production of foods and pharmaceuticals may be used. As a few examples there may be mentioned a fluidized bed granulating method wherein the liquid composition of the disclosure is sprayed onto a fluidized bed that has been fluidized by heated updraft as necessary and then dried, a stirring granulating method wherein the liquid composition of the disclosure is dropped or sprayed onto a fluidized bed that is stirred with a stirring blade or the like, or a freeze drying method.

The liquid composition of the disclosure may be subjected to drying and solidification methods such as spray drying, spray cooling, freeze drying or the like, without addition of a carrier, for solidification such as powderization, to obtain a satisfactory solid composition that can form a fine stable aqueous composition when dissolved or dispersed in an aqueous liquid. If necessary, it may be adsorbed or supported on a carrier for solidification such as powderization. In this case, any carrier may be used that is orally ingestible and can adsorb or support the liquid composition, and as examples there may be mentioned microcrystalline cellulose, β-cyclodextrin, casein or its salts, gelatin, dextrin, various starches, vegetable gums such as gum arabic, psyllium seed gum, pectin, gum arabic, xanthan gum, guar gum, agar and pullulan, hydroxypropyl cellulose (HPC), sugars (glucose, fructose, sucrose, lactose, reduced maltose and the like), silicon dioxide and sugar alcohols (for example, sorbitol, erythritol, mannitol, xylitol and the like). The carrier may also be appropriately selected to alter the functional properties and characteristics of the obtained solid formulation. For example, using sorbitol, dextrin and/or mannitol as the carrier can further increase the water solubility of the coenzyme $Q_{10}$-containing composition of the disclosure or the product containing it. On the other hand, using lactose, sorbitol and/or crystalline cellulose can produce a plastic deformable composition that can be directly tableted, or a food product containing it, for suitable preparation of chewable tablets, swallowing tablets, tablets to be dissolved before use or effervescent tablets.

The amount of the carrier in the solid composition is in the range of 10-800 parts by weight with respect to 100 parts by weight as the total of the coenzyme $Q_{10}$, glycerin, water-soluble substance and the organic acid used as necessary.

When the composition of the disclosure is added to produce a product such as a food, pharmaceutical, cosmetic or feed, it may be combined with suitable vitamins and the like. As water-soluble vitamins there may be mentioned B group vitamins and vitamin C. The B group vitamins include vitamin $B_1$ derivatives, vitamin $B_2$, vitamin $B_6$, vitamin $B_{12}$, vitamin $B_{13}$, and various vitamin B complexes such as biotin, pantothenic acid, nicotinic acid and folic acid. Vitamin $B_1$ derivatives include all compounds having vitamin $B_1$ physiological activity, such as thiamine and its salts, thiamine disulfide, fursultiamine and its salts, diacethiamine, bisbutytiamine, bisbentiamine, benfotiamine, thiamine monophosphate disulfide, cycotiamine, octotiamine, prosultiamine and the like. As fat-soluble vitamins there may be mentioned vitamin E, vitamin D and its derivatives, vitamin $K_1$, vitamin $K_2$, vitamin A, β-carotene and the like.

According to the disclosure, the amounts of vitamins added may be appropriately set depending on their types, the form of the final product and the desired dosage, but for powder or granules it will normally be in the range of 0.001-30 wt % and preferably 0.01-10 wt %, such as about 1 wt %. For a liquid formulation or beverage it may be in the range of 0.0001-10 wt % and preferably about 0.001-3 wt %.

When the composition of the disclosure is added to prepare various products, it may be combined with added nutrients or nutritional food materials including minerals such as calcium, potassium, iron, zinc and yeast or substances containing them, L-carnitine, creatine, α-lipoic acid, glutathione, glucuronic acid, taurine, collagen, soybean isoflavone, lecithin, peptides, amino acids, γ-aminobutyric acid, diacylglycerol, DHA, EPA, medium chain fatty acid triglycerides, edible fats and oils, capsaicin, chondroitin sulfate, agaricus blazei extract, carrot extract, garlic extract, β-glucan, aojiru, royal jelly, propolis, octacosanol, NADH, D-lipose, ceramide, hyaluronic acid, flavangenol, pycnogenol, maca, chitosan, garcinia extract, chondroitin, glucosamine, and milk proteins such as casein sodium, casein calcium, casein magnesium and the like. In addition, there may be suitably added and combined flavoring components such as sugars, proteins, lipids, dietary fiber, sweeteners, aromas, juices and the like, or aromatic components such as coffee aroma, powdered tea aroma or milk aroma.

As additional components there may be included herbs such as ginkgo leaf extract, grape seed extract and valerian extract, as well as galenicals such as ginseng, while teas such as tochu tea, oolong tea, green tea, black tea and pearl barley tea may also be added.

As food forms to which the composition of the disclosure may be added, there may be mentioned tablets, candy tablets, chewable tablets, powders, capsules, granules or fluid diets such as tube-feeding or enteral nutrients, drinks and other health foods or nutritional supplements, tea beverages such as green tea, oolong tea and black tea, other beverages such as soft drinks, jelly beverages, sports drinks, milk based drinks, carbonated beverages, fruit juices, lactic acid bacteria beverages, fermented milk beverages, powdered beverages, cocoa beverages and purified water, and butter, mayonnaise, shortening, margarine, custard cream, dressings, breads, rices, noodles, miso soup, tofu, milk, pasta, soups and sauces, and desserts such as biscuits and cookies, chocolate, candy, cake, ice cream, chewing gum, tablets and the like, and yogurt. A food of the disclosure may be produced by ordinary methods involving addition of the other food materials used in the production, including various nutrients, vitamins, minerals, dietary fiber or additives, such as gustatory components, sweeteners, acidulants such as organic acids, stabilizers and flavorings.

When the composition of the disclosure is applied as a drug, the dosage form may be tablets, capsules, granules, powder, syrup, suspension, ointment, cream, gel, medical patch or the like. A drug according to the disclosure may be produced according to an ordinary process with addition of commonly used excipients, disintegrators, binders, lubricants, surfactants, alcohols, water, water-soluble macromolecules, sweeteners, taste correctives, acidulants and the like depending on the dosage form. A liquid formulation may be in the form of a solution or suspension in water or another appropriate medium, prepared at the time of use. Tablets and granules may also be coated by known methods.

The composition of the disclosure may also be used as a raw material or stock for feed to produce animal feeds such as livestock feeds or pet foods, for ingestion by animals such as livestock or pets. The composition of the disclosure may also be applied to cosmetics such as creams, milky lotions, lotions, lipsticks and lip creams, in the same manner as for drugs.

A food, drug or feed containing the composition of the disclosure allows coenzyme $Q_{10}$ to be efficiently ingested in an easy and reliable manner at any time and any place. Furthermore, since the coenzyme $Q_{10}$-containing composition is readily water-soluble and has excellent taste properties, it can be easily processed as a food or the like and can be easily ingested by the elderly or by those with dysphagia.

The present disclosure will now be further explained by examples, with the understanding that the disclosure is not limited to the examples.

EXAMPLES

Example 1

After adding 800 g of octenylsuccinate starch sodium (Matsutani Chemical Industry Co., Ltd.), 300 g of dextrin (Matsutani Chemical Industry Co., Ltd.) and 100 g of glycerin to 4000 g of purified water, the mixture was heated to about 60° C. To this there was added 800 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured using a laser diffraction/scattering particle size distribution analyzer (MICROTRAC FRA; Nikkiso Co., Ltd.) and the 50% particle size was found to be 0.31 μm.

Next, the emulsion was ejected into a hot air stream heated to 180° C. to remove the moisture, thereby obtaining an orange powdered composition containing 40 wt % of coenzyme $Q_{10}$.

Example 2

After adding 800 g of octenylsuccinate starch sodium (Matsutani Chemical Industry Co., Ltd.), 300 g of dextrin (Matsutani Chemical Industry Co., Ltd.), 60 g of glycerin and 40 g of malic acid to 4000 g of purified water, the mixture was heated to about 60° C. To this there was added 800 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.41 μm.

An orange powdered composition containing 40 wt % of coenzyme $Q_{10}$ was then obtained from the emulsion in the same manner as Example 1.

Example 3

After adding 240 g of octenylsuccinate starch sodium (Matsutani Chemical Industry Co., Ltd.), 120 g of dextrin (Matsutani Chemical Industry Co., Ltd.) and 24 g of glycerin to 1200 g of purified water, the mixture was heated to about 60° C. To this there was added 416 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.39 μm.

An orange powdered composition containing 52 wt % of coenzyme $Q_{10}$ was then obtained from the emulsion in the same manner as Example 1.

Example 4

After adding 240 g of octenylsuccinate starch sodium (Matsutani Chemical Industry Co., Ltd.), 80 g of dextrin (Matsutani Chemical Industry Co., Ltd.), 40 g of gum arabic (Ina Food Industry Co., Ltd.) and 24 g of glycerin to 1200 g of purified water, the mixture was heated to about 60° C. To this there was added 416 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.48 μm.

An orange powdered composition containing 52 wt % of coenzyme $Q_{10}$ was then obtained from the emulsion in the same manner as Example 1.

Example 5

After adding 240 g of octenylsuccinate starch sodium (Matsutani Chemical Industry Co., Ltd.), 104 g of dextrin (Matsutani Chemical Industry Co., Ltd.), 24 g of glycerin and 16 g of malic acid to 1200 g of purified water, the mixture was heated to about 60° C. To this there was added 416 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.44 μm.

An orange powdered composition containing 52 wt % of coenzyme $Q_{10}$ was then obtained from the emulsion in the same manner as Example 1.

Example 6

A 400 g portion of the emulsion obtained in Example 5 was powdered on a fluidized bed using 2400 g of dextrin (Sanwa Cornstarch Co., Ltd.) as a carrier, to obtain an orange powdered-granulated powder composition.

Example 7

A 400 g portion of the emulsion obtained in Example 5 was powdered on a fluidized bed using 1800 g of dextrin (Sanwa Cornstarch Co., Ltd.) and 600 g of sorbitol (Nikken Fine Chemicals Co., Ltd.) as carriers, to obtain an orange powdered-granulated powder composition.

Comparative Example 1

After adding 800 g of octenylsuccinate starch sodium (Matsutani Chemical Industry Co., Ltd.) and 400 g of dextrin (Matsutani Chemical Industry Co., Ltd.) to 4000 g of purified water, the mixture was heated to about 60° C. To this there was added 800 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.33 μm.

The emulsion was then ejected into a hot air stream heated to 180° C. to remove the moisture, thereby obtaining an orange powdered composition (solid formulation).

Comparative Example 2

After adding 240 g of octenylsuccinate starch sodium (Matsutani Chemical Industry Co., Ltd.) and 144 g of dextrin (Matsutani Chemical Industry Co., Ltd.) to 1200 g of purified water, the mixture was heated to about 60° C. To this there was added 416 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.39 μm.

An orange powdered composition was then obtained from the emulsion in the same manner as Comparative Example 1.

Comparative Example 3

After adding 240 g of octenylsuccinate starch sodium (Matsutani Chemical Industry Co., Ltd.) and 240 g of dextrin (Matsutani Chemical Industry Co., Ltd.) to 1200 g of purified water, the mixture was heated to about 60° C. To this there was added 320 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.45 μm.

An orange powdered composition was then obtained from the emulsion in the same manner as Comparative Example 1.

Comparative Example 4

After adding 140 g of octenylsuccinate starch sodium (Matsutani Chemical Industry Co., Ltd.), 200 g of dextrin (Matsutani Chemical Industry Co., Ltd.) and 140 g of lactose (DMV International) to 1400 g of purified water, the mixture was heated to about 60° C. To this there was added 320 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.63 μm.

An orange powdered composition was then obtained from the emulsion in the same manner as Comparative Example 1.

Comparative Example 5

After adding 800 g of gum arabic (Ina Food Industry Co., Ltd.), 340 g of dextrin (Matsutani Chemical Industry Co., Ltd.) and 60 g of glycerin to 4000 g of purified water, the mixture was heated to about 60° C. To this there was added 800 g of coenzyme $Q_{10}$ (Nisshin Pharma Inc.), and the mixture was stirred and passed through a high-pressure homogenizer (treatment pressure: 700 kg/cm$^2$, 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.64 μm.

An orange powdered composition was then obtained from the emulsion in the same manner as Comparative Example 1.

Comparative Example 6

After adding 800 g of octenylsuccinate starch sodium (Matsutani Chemical Industry Co., Ltd.), 340 g of gum arabic (Ina Food Industry Co., Ltd.) and 60 g of glycerin to 4000 g of purified water, the mixture was heated to about 60° C. To this there was added 800 g of coenzyme $Q_{10}$ (Nisshin Pharma Inc.), and the mixture was stirred and passed through a high-pressure homogenizer (treatment pressure: 700 kg/cm², 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.81 μm.

An orange powdered composition was then obtained from the emulsion in the same manner as Comparative Example 1.

Comparative Example 7

After adding 690 g of dextrin (Matsutani Chemical Industry Co., Ltd.), 50 g of lecithin, 400 g of soybean oil and 60 g of glycerin to 4000 g of purified water, the mixture was heated to about 60° C. To this there was added 800 g of coenzyme $Q_{10}$ (Nisshin Pharma Inc.), and the mixture was stirred and passed through a high-pressure homogenizer (treatment pressure: 700 kg/cm², 3 times) to obtain a homogeneous emulsion.

The particle size of the dispersed emulsified coenzyme $Q_{10}$-containing particles in the emulsion was measured in the same manner as Example 1 and the 50% particle size was found to be 0.72 μm.

An orange powdered composition was then obtained from the emulsion in the same manner as Comparative Example 1. However, problems occurred from the standpoint of handleability in that the oil components caused sticking during spray drying of the emulsion.

Comparative Example 8

After adding 740 g of corn starch, 400 g of dextrin and 60 g of glycerin to 4000 g of purified water, the mixture was heated to about 60° C. To this there was added 800 g of coenzyme $Q_{10}$ (Nisshin Pharma Inc.), and the mixture was stirred and passed through a high-pressure homogenizer (treatment pressure: 700 kg/cm², 3 times). However, although an emulsion was formed immediately after treatment, it rapidly separated and it was not possible to maintain a homogeneous emulsion.

Comparative Example 9

After adding 400 g of hydroxypropyl starch (Nippon Starch Chemical Co., Ltd.), 340 g of dextrin (Matsutani Chemical Industry Co., Ltd.), 400 g of casein sodium and 60 g of glycerin to 4000 g of purified water, the mixture was heated to about 60° C. To this there was added 800 g of coenzyme $Q_{10}$ (Nisshin Pharma Inc.), and the mixture was stirred and passed through a high-pressure homogenizer (treatment pressure: 700 kg/cm², 3 times) to obtain a fine, homogeneous emulsion.

The particle size of the dispersed emulsified coenzyme $Q_{10}$-containing particles in the emulsion was measured in the same manner as Example 1 and the 50% particle size was found to be 0.75 μm.

An orange powdered composition containing 40 wt % of coenzyme $Q_{10}$ was then obtained from the emulsion in the same manner as Comparative Example 1.

Comparative Examples 10-12

A coenzyme $Q_{10}$-containing emulsion was obtained in the same manner as Comparative Example 9, except that acetylated phosphoric acid crosslinked starch (Comparative Example 10), acetylated oxidized starch (Comparative Example 11) or hydroxypropylated phosphoric acid crosslinked starch (Comparative Example 12) was used instead of the hydroxypropyl starch in Comparative Example 9. The 50% particle sizes of the dispersed emulsified coenzyme $Q_{10}$-containing particles in the emulsions were 0.62 μm (Comparative Example 10), 0.55 μm (Comparative Example 11) and 0.48 μm (Comparative Example 12).

Orange powdered compositions containing 40 wt % of coenzyme $Q_{10}$ were then obtained from the emulsions in the same manner as Comparative Example 1.

Test Example 1

Emulsion Stability Test

After dispersing 1 g of each coenzyme $Q_{10}$-containing powdered composition of Examples 1, 2, 3 and 5 and Comparative Examples 1-4 in 100 ml of water, the mean particle size of the dispersion was measured using a laser diffraction/scattering particle size distribution analyzer (MICROTRAC FRA; Nikkiso Co., Ltd.). The ease of dispersion in water was evaluated by visual observation. The obtained results are shown in Table 1 below. The mean particle sizes (μm) are shown in the upper row and the results for the ease of dispersion as evaluated based on the following scale are shown in the lower row.
−: Satisfactorily dispersed
+: Time required for dispersion
++: Considerable time required for dispersion
(40° C. glass bottle packing), Upper row: mean particle size (μm)

TABLE 1

| | Storage period | | | |
|---|---|---|---|---|
| Sample | Initial | Week 2 | Week 4 | Week 6 |
| Example 1 | 0.31 | 0.30 | 0.32 | 0.36 |
| | − | − | − | − |
| Example 2 | 0.41 | 0.43 | 0.42 | 0.44 |
| | − | − | − | − |
| Example 3 | 0.39 | 0.40 | 0.39 | 0.42 |
| | − | − | − | − |
| Example 5 | 0.44 | 0.46 | 0.45 | 0.49 |
| | − | − | − | − |
| Comp. Ex. 1 | 0.33 | 0.48 | 0.98 | 1.58 |
| | + | + | ++ | ++ |
| | | | | (precipitated) |
| Comp. Ex. 2 | 0.39 | 0.52 | 1.06 | 1.62 |
| | + | + | ++ | ++ |
| | | | | (precipitated) |
| Comp. Ex. 3 | 0.45 | 0.60 | 1.29 | 1.75 |
| | + | + | ++ | ++ |
| | | | | (precipitated) |
| Comp. Ex. 4 | 0.63 | 0.81 | 1.59 | 2.03 |
| | + | + | ++ | ++ |
| | | | | (precipitated) |

The results in Table 1 indicate that in Examples 1, 2, 3 and 5 that contained combinations of octenylsuccinate starch, dextrin and glycerin, the aqueous dispersion was highly satisfactory compared to Comparative Examples 1-4 that had one or two components of the combinations replaced with other components, and their states of dispersion were also satisfactorily maintained during prolonged storage. In addition, the mean particle sizes of the examples at the time of aqueous dispersion were also satisfactorily maintained during prolonged storage. However, Comparative Examples 1-4 exhibited an increase in the mean particle size at the time of aqueous dispersion during prolonged storage, with precipitation occurring within 6 weeks of storage and problems with aqueous dispersibility becoming apparent after prolonged storage.

These results confirmed that the composition of the disclosure has very excellent aqueous dispersibility even after prolonged storage, despite its high coenzyme $Q_{10}$ content, and that the mean particle size at the time of aqueous dispersion is also stably maintained.

Test Example 2

Coenzyme $Q_{10}$ Stability Test

The residual ratio of coenzyme $Q_{10}$ was measured in each of the dispersions obtained by dispersing 1 g of the powdered compositions of Examples 1, 2, 3 and 5 and Comparative Examples 1 and 2 in 100 ml of water.

1) Storage Conditions

Storage temperature: 50° C.; sealed glass bottle, storage for 0-6 weeks

2) Measurement was Conducted by HPLC Under the Following Conditions.

Detector: Ultraviolet absorptiometer (measuring wavelength: 275 nm)

Column: Hypersil ODS-5 4.6 mm×15 cm, Mobile phase: methanol/anhydrous ethanol (13:7)

The residual ratios (%) are shown in Table 2, with 100% defined as the ratio at the start of glass bottle packing.

TABLE 2

| Sample | Storage period | | | |
|---|---|---|---|---|
| | Initial | Week 2 | Week 4 | Week 6 |
| Example 1 | 100.0 | 99.9 | 98.0 | 97.8 |
| Example 2 | 100.0 | 99.8 | 99.9 | 99.6 |
| Example 3 | 100.0 | 98.8 | 97.7 | 97.7 |
| Example 5 | 100.0 | 100.1 | 99.9 | 99.7 |
| Comp. Ex. 1 | 100.0 | 97.9 | 93.9 | 88.9 |
| Comp. Ex. 2 | 100.0 | 98.1 | 94.4 | 89.5 |

The results in Table 2 indicate that in Examples 1, 2, 3 and 5, the coenzyme $Q_{10}$ in the composition was essentially resistant to decomposition even after prolonged storage, and was therefore stably maintained. In Comparative Examples 1 and 2, however, the coenzyme $Q_{10}$ residual ratios began to fall from 4 weeks after storage, reaching a coenzyme $Q_{10}$ loss of about 10% by the end of 6 weeks, and therefore the storage stability was unsatisfactory. These results confirmed that the composition of the disclosure has notably superior coenzyme $Q_{10}$ storage stability despite its high coenzyme $Q_{10}$ content.

Test Example 3

Emulsion/Coenzyme $Q_{10}$ Stability Test

The coenzyme $Q_{10}$-containing powdered composition of Example 1 and the coenzyme $Q_{10}$-containing powdered compositions of Comparative Examples 5, 6, 7, 9, 10, 11 and 12 were evaluated for emulsion stability of the composition after redispersion in water and for coenzyme $Q_{10}$ stability in the compositions, in the same manner as in Test Examples 1 and 2. The results are shown in Tables 3 and 4 below.

TABLE 3

| Sample | Storage period | | | |
|---|---|---|---|---|
| | Initial | Week 2 | Week 4 | Week 6 |
| Example 1 | 0.31 | 0.30 | 0.32 | 0.36 |
| | − | − | − | − |
| Comp. Ex. 5 | 0.64 | 0.88 | 1.43 | 1.91 |
| | + | + | ++ | ++ (precipitated) |
| Comp. Ex. 6 | 0.81 | 0.98 | 1.29 | 1.78 |
| | + | + | ++ | ++ (precipitated) |
| Comp. Ex. 7 | 0.72 | 0.96 | 1.33 | 1.50 |
| | + | + | ++ | ++ (precipitated) |
| Comp. Ex. 9 | 0.75 | 0.82 | 1.56 | 2.12 |
| | + | + | ++ (precipitated) | ++ (precipitated) |
| Comp. Ex. 10 | 0.62 | 0.73 | 1.35 | 1.87 |
| | + | + | ++ | ++ (precipitated) |
| Comp. Ex. 11 | 0.55 | 0.71 | 1.33 | 1.88 |
| | + | + | ++ | ++ (precipitated) |
| Comp. Ex. 12 | 0.48 | 0.69 | 1.21 | 2.32 |
| | + | + | ++ | ++ (precipitated) |

TABLE 4

| Sample | Storage period | | | |
|---|---|---|---|---|
| | Initial | Week 2 | Week 4 | Week 6 |
| Example 1 | 100.0 | 99.9 | 98.0 | 97.8 |
| Comp. Ex. 5 | 100.0 | 96.8 | 92.9 | 89.5 |
| Comp. Ex. 6 | 100.0 | 95.8 | 93.7 | 87.3 |
| Comp. Ex. 7 | 100.0 | 96.1 | 93.9 | 89.7 |
| Comp. Ex. 9 | 100.0 | 97.9 | 94.1 | 87.8 |
| Comp. Ex. 10 | 100.0 | 98.1 | 94.4 | 88.4 |
| Comp. Ex. 11 | 100.0 | 97.3 | 94.1 | 88.7 |
| Comp. Ex. 12 | 100.0 | 96.2 | 93.8 | 88.5 |

The results in Tables 3 and 4 show that the compositions of Comparative Examples 5, 6, 7, 9, 10, 11 and 12 had poor dispersion in water and increased mean particle sizes during dispersion after prolonged storage, compared to the coenzyme $Q_{10}$-containing composition of the disclosure (Example 1). Also, precipitation occurred within 4-6 weeks of storage, and therefore the dispersion stability in water after prolonged storage was unsatisfactory. In addition, the coenzyme $Q_{10}$ residual ratios began to fall from 2-4 weeks after prolonged storage, reaching a content of less than 90% by the end of 6 weeks, and therefore the coenzyme $Q_{10}$ storage stability was unsatisfactory.

Test Example 4

Absorption Test

The powder obtained in Example 1 and the coenzyme $Q_{10}$-containing powder obtained in Comparative Example 3 were filled into hard capsules and supplied for an absorption test. Specifically, two groups of beagles (male), with three in each group, were force-fed a single dose of 90 mg/dog of coenzyme $Q_{10}$. Blood was sampled at predetermined times up to 24 hours after feeding, and the time-dependent changes of coenzyme $Q_{10}$ plasma concentration were examined. The beagles were starved from 5:00 pm on the previous day with supply of water alone, and on the day of the test were force-fed a capsule with 100 ml of water, without morning feeding.

The coenzyme $Q_{10}$ was measured by HPLC under the following conditions. Since oxidized and reduced forms of coenzyme $Q_{10}$ are present in the serum, the total of both was calculated.
Column: Nucleosil 5C18 4.6 mm×25 cm
Mobile phase: ethanol:acetonitrile (55:45)
Flow rate: 1 ml/min
Detector: Ultraviolet spectrophotometer, 275 nm
Temperature: 35° C., Injection volume: 5 μL Each obtained coenzyme $Q_{10}$ blood concentration was used to determine the maximum blood concentration, time to maximum blood concentration and area under the blood concentration-time curve, as pharmacokinetic parameters. The results are shown in Table 5 below.

TABLE 5

|  | Cmax (μg/ml) | tmax (hr) | AUC (0→t) (μg/hr/ml) |
| --- | --- | --- | --- |
| Example 1 | 0.917 ± 0.98 | 6.0 ± 1.8 | 8.31 ± 0.47 |
| Comp. Ex. 3 | 0.362 ± 0.87 | 6.3 ± 2.4 | 3.12 ± 0.63 |

(Mean ± S.D.)
Cmax (μg/ml): Maximum blood concentration
tmax (hr): Time at which maximum blood concentration reached
AUC (0→t)(μg/hr/ml): Area under blood concentration-time curve The results of this absorption test confirmed that, based on coenzyme $Q_{10}$ plasma concentration, the composition of Example 1 allows a high level of coenzyme $Q_{10}$ to be absorbed in the body reliably even when orally administered after fasting, as compared to the composition of Comparative Example 3. This demonstrated that the composition of the disclosure has highly superior bioavailability.

Example 8

After mixing 430 g of soybean oil (Yoshihara Seiyu) and 20 g of glycerin fatty acid ester (Riken Vitamin Co., Ltd.), the mixture was heated to about 65° C. for dissolution. It was then cooled to room temperature, 150 g of the powdered composition of Example 2 was added, and the mixture was stirred to prepare a filling solution. The filling solution was used to prepare soft capsules with 300 mg per capsule by an ordinary soft capsule forming procedure. The capsules contained 30 mg of coenzyme $Q_{10}$.

Example 9

After mixing 100 g of L-carnitine/L-tartrate, 260 g of crystalline cellulose (Asahi Kasei Corp.), 80 g of lactose (DMV International) and 10 g of HPC (hydroxypropyl cellulose) (Nippon Soda Co., Ltd.), the mixture was kneaded for 5 minutes in a kneader with 80 mL of ethanol by an ordinary method. Upon completion of the kneading, the mixture was passed through a 10 mesh filter and dried at 50° C. with a drier. After drying, it was granulated to obtain granules. To the granules there was added 150 g of the powdered composition of Example 2 to obtain a coenzyme $Q_{10}$-containing granule product. The granules were stick-packed at 1.2/pack, to obtain granules containing 120 mg of coenzyme $Q_{10}$ per stick.

Example 10

After mixing 222 g of crystalline cellulose (Asahi Kasei Corp.), 200 g of lactose (DMV International) and 18 g of HPC (hydroxypropyl cellulose) (Nippon Soda Co., Ltd.), the mixture was kneaded for 5 minutes in a kneader with 130 mL of ethanol by an ordinary method. Upon completion of the kneading, the mixture was passed through a 16 mesh filter and dried at 50° C. with a drier. After drying, it was granulated to obtain granules. To the granules there was added 10 g of sucrose fatty acid ester (Mitsubishi Chemical Corp.), and after mixing for 1 minute, 150 g of the powdered composition of Example 2 was added and mixing was continued to prepare a tableting powder. The powder was tableted using a tableting machine to prepare tablets at 300 mg each. The tablets contained 30 mg of coenzyme $Q_{10}$ per tablet.

Example 11

After mixing 250 g of the powdered composition obtained in Example 2, 580 g of crystalline cellulose (Asahi Kasei Corp.) and 130 g of reduced maltose (Nikken Fine Chemicals Co., Ltd.), there was added 40 g of sucrose fatty acid ester (Mitsubishi Chemical Corp.) and the components were mixed to prepare a tableting powder. The powder was tableted using a tableting machine to prepare tablets at 500 mg each. The tablets contained 50 mg of coenzyme $Q_{10}$ per tablet.

Example 12

After stirring 1.0 g of citric acid (Tanabe Seiyaku Co., Ltd.) and 200 g of glucose solution (Nihon Shokuhin Kako Co., Ltd.) in 649 g of purified water until dissolution, the pH was adjusted to 3.0-3.5. There was then added 150 g of the powdered composition of Example 2 to dissolution to obtain a homogeneous beverage composition containing coenzyme $Q_{10}$.

Example 13

Through a 16 mesh filter there were passed 225 g of the powdered composition of Example 2, 15 g of vitamin $B_1$, 30 g of L-carnitine/L-tartrate, 390 g of crystalline cellulose (Asahi Kasei Corp.), 230 g of lactose 200M (DMV International) and 10 g of citric acid (Tanabe Seiyaku Co., Ltd.), to obtain a powder. The powder was filled into No. 2 hard capsules at about 300 mg per capsule (30 mg coenzyme $Q_{10}$ content per capsule) to obtain coenzyme $Q_{10}$-containing hard capsules.

Example 14

There were combined 120 g of wheat flour (strong flour) and 2 g of dry yeast. Also, 2.5 g of the powdered composition of Example 2, 20 g of sugar, 3 g of salt and 6 g of skim milk powder were dissolved in 70 g of hot water, one egg was added and the mixture was thoroughly stirred, after which 8 g of malic acid was added and stirring was continued. The mixture was added to wheat flour and thoroughly kneaded by hand, after which about 40 g of butter was added prior to further kneading to obtain dough for 20 bread rolls. After subsequent fermentation, lightly beaten egg was spread over the surface and the dough was baked for about 12 minutes in an oven at 180° C. to obtain bread rolls. The bread rolls contained about 50 mg of coenzyme $Q_{10}$ each.

Example 15

There were mixed 200 g of wheat flour (strong flour) and 4 g of dry yeast. In addition, 2.5 g of the powdered composition of Example 2, 10 g of sugar, 4 g of salt, 10 g of skim milk and 15 g of shortening were dissolved in 150 g of water, and both were thoroughly mixed. After subsequent fermentation, the mixture was baked for about 15 minutes in an oven at 150° C. to produce 10 bread loaves. The bread loaves contained about 1000 mg of coenzyme $Q_{10}$ each.

Example 16

One serving of pasta meat sauce (150 g) was placed in a pot, and then 150 mg of the powdered composition of Example 2 (corresponding to 60 mg of coenzyme $Q_{10}$) was added and the mixture was stirred while heating to obtain pasta meat sauce containing coenzyme $Q_{10}$. The sauce was filled into a pouch, and then the pouch was sealed with nitrogen replacement and sterilized at 121° C. for 15 minutes to obtain coenzyme $Q_{10}$-containing pasta meat sauce.

Example 17

After adding two of the coenzyme $Q_{10}$-containing soft capsules produced in Example 8 (corresponding to 60 mg of coenzyme $Q_{10}$) to two "go" volumes of rice, it was boiled with a sufficient amount of water and filled into a retort pouch according to a common method, after which the pouch was sealed with nitrogen replacement and sterilized at 121° C. for 15 minutes to obtain retort boiled rice. The retort boiled rice contained about 30 mg of coenzyme $Q_{10}$ per serving, and had a satisfactory appearance, taste and texture.

Example 18

After dispersing 375 mg of the powdered composition of Example 2 and 15 g of salt in 150 g of water, the dispersion was thoroughly kneaded with 300 g of wheat flour (all-purpose flour) and allowed to stand. Next, the dough was spread and cut to a width of about 5 mm to produce three servings of noodles. These were then boiled for about 10 minutes in boiling water, yielding noodles with a satisfactory appearance, taste and texture. The noodles contained about 50 mg of coenzyme $Q_{10}$ per serving.

Example 19

After mixing 200 mL of milk, 4.5 g of gelatin, 45 g of sugar and 15 g of water, the mixture was heated on a flame for complete dissolution of the gelatin. After confirming dissolution, 0.3 g of the powdered composition of Example 2 (0.12 g of coenzyme $Q_{10}$) was thoroughly mixed and dissolved therewith. The mixture was then poured into four cups and cooled to hardness for at least 2 hours in a refrigerator to obtain milk jelly. The milk jelly contained about 30 mg of coenzyme $Q_{10}$ per cup.

Example 20

Upon thoroughly mixing 15 g of the powdered composition of Example 2 and 585 g of powdered organic aojiru (Nisshin Pharma Inc.), there was obtained stick packs containing approximately 3 g per serving.
The powdered aojiru contained about 30 mg of coenzyme $Q_{10}$ per stick.

Example 21

A beverage was obtained by dissolving 1.5 g of the powdered composition of Example 2 in 1 L of oolong tea. The tea contained about 60 mg of coenzyme $Q_{10}$ per 100 mL.
Industrial Applicability According to the present disclosure there is provided a coenzyme $Q_{10}$-containing composition having a high coenzyme $Q_{10}$ content and excellent coenzyme $Q_{10}$ stability and bioavailability (absorption, bioutility, etc.) without using synthetic emulsifiers such as glycerin fatty acid esters. A liquid composition of the disclosure can maintain a satisfactory emulsified state even with prolonged storage, despite its high coenzyme $Q_{10}$ content. Furthermore, a solid composition of the disclosure is suitable as it can form a fine and stable aqueous composition by addition to an aqueous liquid such as water without loss of dissolution or dispersion properties in the aqueous liquid, even when stored for prolonged periods. It is a feature of the composition that it allows reliable absorption of coenzyme $Q_{10}$ even on an empty stomach. Consequently, the composition of the disclosure can be added and combined with various forms of foods and drinks, drugs, cosmetics and feeds to provide high bioavailability of coenzyme $Q_{10}$.

What is claimed is:
1. A coenzyme $Q_{10}$-containing solid composition, wherein said coenzyme $Q_{10}$-containing solid composition is produced by the following steps:
 a) dispersing and emulsifying:
  1-50 wt % of coenzyme $Q_{10}$;
  0.01-10 wt % of glycerin;
  4-30 wt % of octenylsuccinate starch and dextrin; and
  40-94 wt % of water,
  thereby forming an emulsified coenzyme $Q_{10}$-containing liquid composition,
 b) forming a homogeneous emulsified coenzyme $Q_{10}$-containing liquid composition comprised of dispersed and emulsified particles of step a) containing coenzyme $Q_{10}$, wherein said particles containing coenzyme $Q_{10}$ have a mean particle size that is no greater than 3 μm; and
 c) drying said coenzyme $Q_{10}$-containing liquid composition formed in step (b), to form an ingestible coenzyme $Q_{10}$-containing solid composition.
2. The coenzyme $Q_{10}$-containing solid composition according to claim 1, comprising:
 3-80 wt % of coenzyme $Q_{10}$;
 0.01-25 wt % of glycerin; and
 19-96 wt % of octenylsuccinate starch and dextrin.
3. The coenzyme $Q_{10}$-containing solid composition according to claim 1, wherein said particles containing coenzyme $Q_{10}$ in said coenzyme $Q_{10}$-containing solid composition maintain a mean particle size that is no greater than 3 μm after re-dispersion in water.
4. The coenzyme $Q_{10}$-containing solid composition according to claim 1, wherein said particles containing coenzyme $Q_{10}$ have a mean particle size that is no greater than 0.8 μm.
5. The coenzyme $Q_{10}$-containing solid composition according to claim 4, wherein said particles containing coenzyme $Q_{10}$ in said coenzyme $Q_{10}$-containing solid composition maintain a mean particle size that is no greater than 0.8 μm after re-dispersion in water.
6. The coenzyme $Q_{10}$-containing solid composition according to claim 1, wherein said particles containing coenzyme $Q_{10}$ in said coenzyme $Q_{10}$-containing solid composition are readily water-soluble.
7. The coenzyme $Q_{10}$-containing solid composition according to claim 1, wherein the amount of coenzyme $Q_{10}$ is 13-50 wt %.
8. The coenzyme $Q_{10}$-containing solid composition according to claim 1, wherein said particles containing coenzyme $Q_{10}$ in said coenzyme $Q_{10}$-containing solid composi- tion have a residual ratio greater than 95% after re-dispersion in water and a storage period of six weeks.

9. A food, pharmaceutical, or feed containing a coenzyme $Q_{10}$-containing solid composition, wherein said coenzyme $Q_{10}$-containing solid composition is produced by the following steps:
   a) dispersing and emulsifying:
      1-50 wt % of coenzyme $Q_{10}$;
      0.01-10 wt % of glycerin;
      4-30 wt % of octenylsuccinate starch and dextrin; and
      40-94 wt % of water,
      thereby forming an emulsified coenzyme $Q_{10}$-containing liquid composition,
   b) forming a homogeneous emulsified coenzyme $Q_{10}$-containing liquid composition comprised of dispersed and emulsified particles of step (a) containing coenzyme $Q_{10}$,
   wherein said particles containing coenzyme $Q_{10}$ have a mean particle size that is no greater than 3 μm; and
   c) drying said coenzyme $Q_{10}$-containing liquid composition formed in step (b), to form an ingestible coenzyme $Q_{10}$-containing solid composition.

10. The food, pharmaceutical, or feed according to claim 9, wherein said coenzyme $Q_{10}$-containing solid composition comprises:
    3-80 wt % of coenzyme $Q_{10}$;
    0.01-25 wt % of glycerin; and
    19-96 wt % of octenylsuccinate starch and dextrin.

11. A process for producing a coenzyme $Q_{10}$-containing solid composition, comprising:
    a) dispersing and emulsifying:
       1-50 wt % of coenzyme $Q_{10}$ in an aqueous liquid containing 0.01-10 wt % of glycerin;
       4-30 wt % of octenylsuccinate starch and dextrin; and
       40-94 wt % of water,
       to prepare a coenzyme $Q_{10}$-containing liquid composition; and
    b) drying said coenzyme $Q_{10}$-containing liquid composition prepared in step (a), to form an ingestible coenzyme $Q_{10}$-containing solid composition.

12. The process for producing the coenzyme $Q_{10}$-containing solid composition according to claim 11, wherein said coenzyme $Q_{10}$-containing solid composition comprises:
    3-80 wt % of coenzyme $Q_{10}$;
    0.01-25 wt % of glycerin; and
    19-96 wt % of octenylsuccinate starch and dextrin.

* * * * *